United States Patent [19]
Parten

[11] Patent Number: 6,143,926
[45] Date of Patent: Nov. 7, 2000

[54] PROCESS FOR PRODUCING PURE TEREPHTHALIC ACID WITH IMPROVED RECOVERY OF PRECURSORS, SOLVENT AND METHYL ACETATE

[75] Inventor: William David Parten, Stockton on Tees, United Kingdom

[73] Assignee: E. I. du Pont de Nemours and Company, Wilmington, Del.

[21] Appl. No.: 09/400,035

[22] Filed: Sep. 21, 1999

[51] Int. Cl.⁷ .................................................. C07C 51/16
[52] U.S. Cl. ............................................ 562/414; 562/412
[58] Field of Search ..................................... 562/412, 414

[56] References Cited

U.S. PATENT DOCUMENTS 2,833,816   5/1958   Saffer et al. .
4,500,732   2/1985   Petty-Weeks et al. .

*Primary Examiner*—Paul J. Killos
*Attorney, Agent, or Firm*—Charles E. Krukiel

[57] ABSTRACT

Process for producing pure terephthalic acid having improved means for recovering and/or recycling terephthalic acid precursors, residual acetic acid and other reaction by-products, such as methyl acetate.

1 Claim, 1 Drawing Sheet

PROCESS FOR PRODUCING PURE TEREPHTHALIC ACID WITH IMPROVED RECOVERY OF PRECURSORS, SOLVENT AND METHYL ACETATE

BACKGROUND OF THE INVENTION

The present invention relates to a continuous integrated process for producing pure terephthalic acid, and, more particularly, to an integrated process having improved means for recovering and/or recycling terephthalic acid precursors, residual acetic acid and other reaction by-products, such as methyl acetate.

Terephthalic acid is produced commercially in a two-stage process which begins with air (molecular oxygen) oxidation of paraxylene in the presence of a metal bromide catalyst system in acetic acid solvent. A crude, i.e., impure, terephthalic acid product is isolated from a slurry in the oxidation stage, usually as a dry crystalline powder. The crude terephthalic acid is recovered from the slurry in the form of a wet cake which is washed as necessary with acetic acid or water. The wet cake is then sent to a dryer where any adherent solvent is removed to form crude terephthalic acid. Water is produced as a significant by-product of the oxidation reaction and is removed from the reaction zone in a reaction off-gas stream. The off-gas stream also includes acetic acid and low levels of methyl acetate, which is a reaction by-product which can result from oxidation of acetic acid. A preferred means for separating and recovering the acetic acid from the off-gas stream for recycle is through azeotropic distillation of the off-gas stream condensate using an organic entrainer selected from, for example, n-butyl acetate, n-propyl acetate and isobutyl acetate. In such cases where the main feed to the azeotropic distillation process is derived from the oxidation reaction overheads, the presence of methyl acetate in the feed stream can adversely affect the amount of water which can be removed from the condensate azeotropically because methyl acetate's water azeotrope lies in the single phase region, i.e. its water azeotrope will have a low water content.

In the second stage of the process, i.e., the purification stage, crude terephthalic acid crystals are dissolved in water at elevated pressure and temperature, and the resulting solution is subjected to hydrogenation in the presence of a Group VIII Noble metal hydrogenation catalyst. The purified acid is recovered by crystallizing the acid from the hydrogen treated aqueous solution. A majority of the principal impurities, which are p-toluic acid derived from the compound 4-carboxybenzaldehyde and unidentified color bodies, along with some other organic components, such as benzoic acid and residual terephthalic acid, remain dissolved in the aqueous solution. This aqueous solution which remains is referred to as "pure plant mother liquor", i.e., PPML. More recent commercial two-stage processes, however, have sought to eliminate the need to recover the crude terephthalic acid as a separate dry product. Instead, the process has undergone degrees of integration whereby crude terephthalic acid crystals can be recovered from the slurry formed in the oxidation stage as a wet cake by depositing the slurry on a moving band of filter material. The wet cake is then washed with water or other solvent according to a predetermined series of washing steps, and then it can be re-dissolved almost immediately in water for purification without the need for a separate drying step.

The integrated process allows for improved economy where it is possible to recover and recycle the resulting pure plant mother liquor. However, under some operating conditions a residual amount of acetic acid can "slip" through the filtration/solvent exchange process, i.e., residual amounts retained within the recovered crude acid, and find its way into the aqueous mother liquor solution. The presence of acetic acid in the pure plant mother liquor can be problematic in attempting to recycle it for use elsewhere in the process. Hence, a method is needed to account for residual acetic acid and methyl acetate levels in the process as well as to provide for recycling residual terephthalic acid, acid precursors and pure plant mother liquor to achieve improved economy from an integrated process.

SUMMARY OF THE INVENTION

The present invention provides an improvement in a continuous process for producing pure terephthalic acid which process comprises the steps of: (a) reacting paraxylene with air in the presence of acetic acid and a catalyst at elevated pressure and temperature to produce crude terephthalic acid; (b) recovering the crude terephthalic acid, including an amount of residual acetic acid and paratoluic acid; and (c) purifying the crude terephthalic acid by mixing it with water and raising the temperature and pressure of the mixture to form an aqueous solution, contacting the aqueous solution with hydrogen in the presence of a catalyst, adjusting the pressure and temperature of the hydrogenated solution whereby pure terephthalic acid crystals precipitate and residual acetic acid and paratoluic acid remain in the hydrogenated solution to form a pure plant mother liquor, and recovering the pure terephthalic acid crystals from the pure plant mother liquor. The improvement comprises:

(i) contacting the pure plant mother liquor with paraxylene to form a two-phase system comprising an aqueous phase which contains residual acetic acid and an organic phase which contains paratoluic acid and paraxylene;

(ii) returning the organic phase to the oxidation reaction of step (a);

(iii) feeding the aqueous phase to at least one additional contacting device simultaneously with a condensate stream comprising water, methyl acetate and organic components to form a second aqueous phase and a second organic phase across which methyl acetate and residual acetic acid partition; and (iv) recovering methyl acetate from the second aqueous phase and recovering acetic acid from the second organic phase.

DETAILED DESCRIPTION OF THE INVENTION

Figure 1:
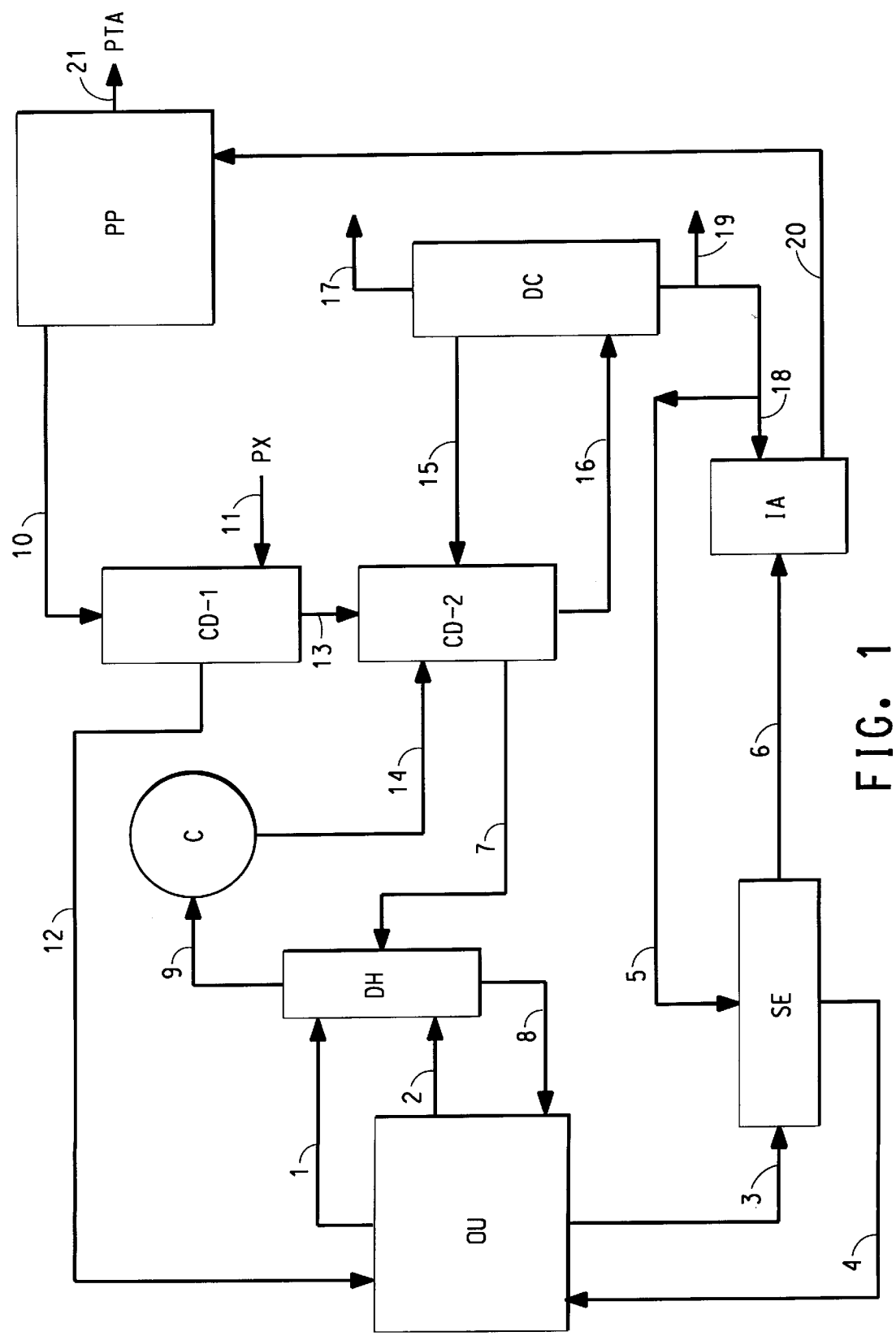
FIG. 1 is a simplified schematic process block diagram for carrying out an embodiment of the invention.

The present invention provides for recycling terephthalic acid precursors, i.e., paratoluic acid, and residual amounts of terephthalic acid left behind in the pure plant mother liquor to the oxidation reaction while controlling levels of methyl acetate and residual acetic acid in a continuous integrated process for producing pure terephthalic acid. The term "integrated" is used herein to mean a conventional two-stage process for producing pure terephthalic acid which has undergone a coupling of the first oxidation stage with the second purification stage to thereby eliminate the need to isolate and recover crude terephthalic acid as a dry crystalline powder from the oxidation stage. Although the invention relates to an integrated process, it can also be applied with satisfactory results to a conventional two-stage process.

The first stage of a typical two-stage process involves the production of impure, i.e., crude, terephthalic acid by liquid phase air (molecular oxygen) oxidation of paraxylene in an aliphatic carboxylic acid solvent, such as acetic acid, using a heavy metal and bromine catalyst as described, for example, in Saffer et al. U.S. Pat. No 2,833,816. The oxidation reaction is accomplished using a stirred reactor, and the reaction is accompanied by the production of an overhead vapor stream comprising water vapor, acetic acid and an amount of methyl acetate. The concentration of the components comprising the reactor overhead vapor stream can vary over a broad range depending on actual operating conditions. Typically the vapor stream will comprise in the range of 69% w/w acetic acid, 12% w/w water, 1% w/w methyl acetate with the balance being largely non-condensible components, such as nitrogen.

FIG. 1 is a simplified schematic process block diagram of a two-stage process for the purposes of illustration. Oxidation of paraxylene is carried out in an oxidation unit 'OU'. The overhead vapor stream is withdrawn from the reactor and cooled within the OU to form a first condensate. Some or all of this first condensate becomes a feed stream shown as line 1 to an azeotropic distillation tower 'DH'. Azeotropic distillation has proven to be an economical method for separating acetic acid from water wherein separation is accomplished in the presence of an organic entrainer selected from, for example, n-butyl acetate, n-propyl acetate and isobutyl acetate. Separation results in a bottoms product comprising around 95% by wt. acetic acid, which is recycled via line 8 to the oxidation reaction, and a tops product comprising water, methyl acetate and organic entrainer. The tops product via line 9 is, in turn, cooled, i.e., condensed, in condenser 'C' to form a second condensate.

Methyl acetate tends to remain in the organic phase and when returned to the azeotropic tower will tend to interfere with the separation of acetic acid from water because the azeotrope of methyl acetate has a low water content and lies in the single phase region. The present invention, therefore, is directed, in part, to controlling the level of methyl acetate in the azeotropic tower.

The oxidation reaction yields a slurry of crude terephthalic acid crystals shown as line 3. The acid crystals can be recovered from the slurry by any suitable solvent exchange means 'SE', such as, for example, by centrifuge(s), rotary drum filter(s) or moving belt filter(s) arranged with re-slurry as appropriate for effective solvent interchange. Regardless of which method is employed for solvent exchange, in practice, crude terephthalic acid crystals are recovered from the slurry, usually in the form of a wet cake, which is then washed at least once, but preferably several times in a series of washing steps, with either pure, i.e., fresh, water or make-up water via line 5 which has been recycled from some other part of the process. The wash water, which now contains a substantial amount of acetic acid solvent, can be recycled to the oxidation reaction via line 4. The recovered crude acid crystals in an integrated process can then be transferred via line 6 and immediately re-dissolved in water to form a solution of impure acid 'IA' to begin the purification stage of the process.

Purification of the crude acid is accomplished by contacting the solution and hydrogen, or a prehumidified hydrogen-containing gas, with a Group VIII Noble metal catalyst in a pure plant 'PP'. Because of its low solubility, terephthalic acid requires either large volumes of water or high temperatures in order to obtain the desired terephthalic acid solution. In practice, the hydrogenation process can be conducted at a temperature within the range of from 200° C. up to the critical temperature of water, i.e., 374° C. Within the preferred temperature range, solutions of about 10% by wt. to about 35% by wt. terephthalic acid are used. Most of the impurities in the impure terephthalic acid are occluded in the acid crystals. By re-dissolving the crude crystals in water (IA) the solution can be transferred via line 20 to the pure plant with the impurities in solution and subject to catalytic hydrogenation treatment.

Pressure conditions for the hydrogenation process depend upon the manner in which the process is conducted. Since the temperature of the solution is substantially above the boiling point of water, and since it is desirable to maintain the aqueous solution in liquid phase, the hydrogenation is carried out in a reactor at a pressure above atmospheric pressure, i.e., typically in the range of from 4000 kPa up to 20,000 kPa. The pressure level is selected to not only maintain the aqueous solution of impure terephthalic acid and hydrogen in liquid phase, but also to prevent premature crystallization of the acid due to minor process variations which can cause vaporization of some of the solvent. This is readily accomplished by use of an inert, non-condensable gas such as nitrogen. By "inert" gas is meant that gas which is not reactive with the terephthalic acid or the hydrogen or solvent.

The hydrogenation process can be practiced using a suitable hydrogenation reactor arranged for intermittent introduction of hydrogen into a bed of catalyst during continuous introduction of the aqueous solution of impure terephthalic acid. The amount of hydrogen used is an excess of the amount required for reduction of the dissolved impurities. Although in practice very little hydrogen is consumed in the hydrogenation, i.e., purification, process of the pure plant PP, the amount of hydrogen used is in the range of from 1 to 7 moles excess above the stoichiometric amount required for the principle reducible impurities, 4-CBA and the characteristically yellow-colored impurities, while making allowance for other impurities of unknown structure. The nature of the end products of all of these impurities is not known but, by optical density measurement of the terephthalic acid product recovered after catalytic hydrogenation treatment via line 21, their absence or reduced concentration can be noted. Severe hydrogenation should be avoided so that conversion of terephthalic acid to such other products as cyclohexane, 1,4-dicarboxylic acid and p-toluic acid does not occur.

The hydrogenation catalyst is preferably a Group VIII Noble metal selected from platinum and/or palladium supported on adsorbent, high surface area charcoal. Reference may be made to any of the standard texts on hydrogenation or catalysts for materials which are catalytically effective under aqueous phase hydrogenation conditions.

The hydrogen treated aqueous solution can be filtered to remove any suspended solids, such as catalyst support fines and extraneous materials of about 5 microns and larger in size. The purified acid is then recovered from the filtered solution conveniently and preferably via crystallization, or via a series of crystallization steps in which the aqueous solution is cooled by releasing the pressure, which, in turn, vaporizes water and dissolved inert gas from the solution, and thereby causes pure terephthalic acid crystals to precipitate leaving pure plant mother liquor as the remaining fluid medium. Following a predetermined number of crystallization steps, the slurry of pure terephthalic acid crystals is fed to a centrifuge, rotating drum filter or other suitable means for separating the pure acid crystals as a wet cake for further processing from the pure plant mother liquor. The pure plant mother liquor, line 10, contains a residual amount of acetic acid along with some useful organic components as well as some dissolved impure terethphalic acid. The present invention, in a second part, is directed to recovering useful organic components and residual acetic acid from the pure plant mother liquor whereby the mother liquor can be made available for recycle.

The invention in its fundamental embodiment comprises contacting the pure plant mother liquor, line 10, with paraxylene, line 11, in suitable contacting decive 'CD-1' to form a two-phase system comprising an aqueous phase which contains residual acetic acid and an organic phase which contains paratoluic acid, i.e. a terephthalic acid precursor, and paraxylene. Paratoluic acid, along with any other precursors which may be present, is transferred from the aqueous environment of the pure plant mother liquor to the organic environment of the paraxylene feed. The organic phase can then be recycled to the oxidation reaction via line 12. The aqueous phase is fed via line 13 to at least one additional contacting device 'CD-2' simultaneously with a condensate stream 14 which comprises water, methyl acetate and organic components to form a second aqueous phase and a second organic phase. Condensate stream 14 results from cooling and condensing in condenser C the overheads vapor stream from the azeotropic column DH, and the organic components therein result primarily from the organic entrainer which is present in the vapor stream. Methyl acetate, the organic components and acetic acid partition across the two phases. In so doing, methyl acetate can be recovered from the resulting aqueous phase by distillation in distillation column 'DC'. The aqueous phase is transferred via line 16 from CD-2 to the distillation column DC, and methyl acetate is recovered from the column overhead via line 17. Water exits the base of DC for either recyle via line 18 or disposal via line 19. Acetic acid and organic entrainer can be recovered from the organic phase by returning, i.e., recycling, the organic phase via line 7 to the azeotropic tower DH as reflux.

Suitable contacting devices for carrying out the solvent extraction process improvements of the invention described above may be decanters, multistage contactors or a series of mixer settler units as described in any of the standard texts. The process of the invention is not to be limited by any specific type of contacting device.

What is claimed is:

1. In a continuous process for producing pure terephthalic acid by (a) first reacting paraxylene with air in the presence of acetic acid and a catalyst at elevated pressure and temperature to produce crude terephthalic acid; (b) recovering the crude terephthalic acid, including an amount of residual acetic acid and paratoluic acid, as a wet cake; and (c) purifying the crude terephthalic acid by mixing it with water and raising the temperature and pressure of the mixture to form an aqueous solution, contacting the aqueous solution with hydrogen in the presence of a catalyst, adjusting the pressure and temperature of the hydrogenated solution whereby pure terephthalic acid crystals precipitate and residual acetic acid and paratoluic acid remain in the hydrogenated solution to form a pure plant mother liquor, and recovering the pure terephthalic acid crystals from the pure plant mother liquor, the improvement comprising:

(i) contacting said pure plant mother liquor with paraxylene to form a two-phase system comprising an aquoues phase which contains residual acetic acid and an organic phase which contains paratoluic acid and paraxylene;

(ii) returning the organic phase to the oxidation reaction of step (a);

(iii) feeding the aqueous phase to at least one additional contacting device simultaneously with a condensate stream comprising water, methyl acetate and organic components to form a second aqueous phase and a second organic phase across which methyl acetate and residual acetic acid partition; and (iv) recovering methyl acetate from the second aqueous phase and recovering acetic acid from the second organic phase.

\* \* \* \* \*